United States Patent [19]

Eckler

[11] Patent Number: 4,847,439

[45] Date of Patent: Jul. 11, 1989

[54] CRYSTALLIZATION-INHIBITED TRIMETHYLOLETHANE SOLUTIONS

[75] Inventor: Paul E. Eckler, Terre Haute, Ind.

[73] Assignee: International Minerals & Chemical Corp., Terre Haute, Ind.

[21] Appl. No.: 83,177

[22] Filed: Aug. 10, 1987

Related U.S. Application Data

[63] Continuation-in-part of Ser. No. 787,621, Oct. 15, 1985, Pat. No. 4,709,104.

[51] Int. Cl.⁴ .................. C07C 29/94; C07C 31/22
[52] U.S. Cl. .................................... 568/853; 568/854
[58] Field of Search ............................... 568/853, 854

[56] References Cited

U.S. PATENT DOCUMENTS 2,292,926  8/1942  Brubaker et al. .................. 568/853

FOREIGN PATENT DOCUMENTS 808878  2/1959  United Kingdom ................ 568/854

*Primary Examiner*—J. E. Evans
*Attorney, Agent, or Firm*—Thomas L. Farquer; Wendell Ray Guffey

[57] ABSTRACT

Crystallization of trimethylolethane from supersaturated aqueous solutions is inhibited in the presence of effective amounts of methanol and formic acid as crystallization inhibitors.

6 Claims, No Drawings

CRYSTALLIZATION-INHIBITED TRIMETHYLOLETHANE SOLUTIONS

CROSS-REFERENCE TO RELATED APPLICATIONS

This application is a continuation-in-part of applicant's U.S. Ser. No. 787,621, filed Oct. 15, 1985, now U.S. Pat. No. 4,709,104.

BACKGROUND AND SUMMARY OF THE INVENTION

This invention relates to a method for inhibiting crystallization of trimethylolethane from supersaturated aqueous solutions thereof and to the crystallization-inhibited solutions prepared in accordance with that method.

Most commercial customers for industrial chemicals prefer to handle bulk raw materials in liquid form. Liquids can be handled economically in bulk by pumping and metering, thus avoiding the manual labor associated with transporting and opening solid-containing containers and weighing solid charges.

Trimethylolethane is a water soluble, crystalline, polyhydric alcohol which finds widespread use in the chemical industry particularly in the manufacture of alkyd resins, drying oils and plasticizers. Trimethylolethane (TME), while a crystalline solid in pure form, is for the above reasons advantageously shipped in bulk for commercial usage as its aqueous solutions. Of course, the more concentrated solutions can be made, the more cost efficient shipping and handling can be. Aqueous solutions of TME as concentrated as 80% solids can be shipped as heated solutions in insulated tank trucks. Aqueous solutions of trimethylolethane at 50% solids can be shipped (as solutions) so long as the outdoor temperatures do not drop below 0°–5° C. Also, 80% by weight solutions are regularly shipped in insulated tank trucks and are stopped in heated tanks. However, crystallization usually begins at about 50° C.

TME is highly soluble in water (140g/100g at 25° C.) and its concentrated aqueous solutions readily become supersaturated as the temperature gradually becomes lower. The term "supersaturated solution" as used herein has the same meaning generally understood in the art, namely a homogeneous solution which contains more of a solute (an excess) than is normally possible at a given temperature. If the solute is normally a solid, a supersaturated solution cannot exist in the presence of a solid phase because the excess dissolved solid promptly comes out of solution as a precipitate and the resulting liquid phase is merely saturated.

The solubility profile of TME in water is such that any cooling of concentrated aqueous TME solutions can easily result in solution supersaturation. Subsequently any crystallization of TME from solution results in reversion of the solution to a saturated one in the presence of the solid phase. Indeed, supersaturated solutions of TME can "crystallize" into a solid crystalline mass. Cooling of concentrated aqueous TME solutions resulting in crystallization during shipment, in storage tanks and in pumping and metering equipment can result in a plant manager's nightmare. There is little that can be done with the resulting solid crystalline mass once it forms in shipping containers or processing equipment except to find some way to heat the "mass" to redissolve the TME, or mechanically to remove the crystallized material from the crystal-clogged equipment It is therefore an object of this invention to provide a method for inhibiting crystallization of TME from supersaturated aqueous solutions of trimethylolethane.

It is a further object of this invention to provide crystallization-inhibited aqueous trimethylolethane solutions and a method for preparing those crystallization-inhibited solutions.

It is still a further object of this invention to identify materials useful as stabilizers (crystallization inhibitors) for aqueous trimethylolethane solutions, and to provide a liquid, pumpable grade of aqueous high solids trimethylolethane solution exhibiting resistance to unwanted, premature crystallization of trimethylolethane from supersaturated solution.

DETAILED DESCRIPTION OF THE INVENTION

In many respects, crystallization is more of an art than a science. Processes based on crystallization steps can be difficult to operate consistently. In some cases crystallizations which have been practiced commercially for extended periods of time can, without warning or explanation, cause difficulties with recovered yields and with crystallization rates. These effects are probably due to trace impurities which inhibit the crystallization process. Generally little is known about these inhibitors but it is logical that the inhibitors somehow interfere with the crystallization process. Often crystallization inhibitors are found by accident and they are nearly always specific to each solid/solvent system. In the case of pentaerythritol, a compound closely related to trimethylolethane, some crystallization inhibitors have been identified, including formaldehyde, sucrose, caustic and trimethylolethane itself.

The present invention is based on applicant's investigation of crystallization inhibitors for supersaturated aqueous trimethylolethane solutions. The concentration of TME in a supersaturated solution varies with the temperature. Generally a solution will be supersaturated at ambient temperatures or below if it contains more than about 50% by weight of TME and no solid phase is present. Of the more than 100 chemical compositions evaluated the following materials were found to be most active as crystallization inhibitors for supersaturated aqueous trimethylolethane solutions: methanol, isopropyl alcohol, 2-ethoxyethanol, 1-methoxy-2-propanol, formaldehyde (methanol inhibited), 1-dimethylamino-2-propanol, and formic acid.

Thus in accordance with the present invention a method is provided for inhibiting crystallization of trimethylolethane from supersaturated aqueous solutions thereof. The method comprises adding methanol or formic acid to the solution, preferably but not necessarily prior to supersaturation in an amount effective to inhibit trimethylolethane crystal formation, namely preferably from about 4 to about 15%, more preferably from about 10 to about 15% of the resulting aqueous trimethylolethane solution. Thus at 5% additive, the composition of the solution would be: additive 5%, TME 50% and water 45%. At 15% additive, the composition would be: additive 15%, TME 45% and water 40.0%.

The crystallization inhibitor can be added to the solution at any time before crystallization occurs, even after supersaturation. Preferably however, it is added while the solution is still at a temperature above saturation temperature. In the process for manufacturing the TME, it is obtained as a dilute solution which is then concentrated by evaporative distillation. When the desired concentration is reached and the solution is still less than saturated, the crystallization inhibitor is added and when supersaturation occurs, the risk of crystallization is minimized.

It is not intended that the amount of inhibitor be limited to 15% or less. Rather any amount above 4% is contemplated, and in severely cold weather, more than 15% may be desirable. However, for most shipping and storage temperatures, between 4% and 15% will be satisfactory.

The invention will be better understood with reference to the following example. It is understood that the example is intended only to illustrate the invention. It is not intended that the invention be limited thereby.

EXAMPLE

The crystallization inhibitors of this invention were identified experimentally by measuring the time needed for solidification on cooling of a 40% aqueous trimethylolethane solution in a freezer at 5° F. Test solutions at the 5% additive level were prepared by combining 2.5 grams of additive with 47.5 grams of a stock solution of 400 grams of trimethylolethane dissolved in 360 ml water. At the 10% level, 5 grams of test additive was combined with 45 grams of a stock solution of 352 grams of trimethylolethane dissolved in 440 ml water. Crystallization inhibitors were identified by those test solutions which failed to solidify after two hours in a freezer at 5° F. Formic acid (88% grade was used for convenience), 1-dimethylamino-2-propanol and formaldehyde (37% aqueous) wholly or partially prevented crystallization in the supersaturated trimethylolethane solution at the 5% level. Compounds found to be effective crystallization inhibitors at the 10% level were methanol, formic acid, 1-dimethylamino-2-propanol, formaldehyde (37%), isopropyl alcohol, 2-ethoxyethanol and 1-methoxy-2-propanol (Dowanol PM). Secondary-butyl alcohol, tertiary-butyl alcohol and 2-methoxyethanol were found to exhibit partial efficacy as a crystallization inhibitor of TME solutions at the 10% by weight level. In the case of formic acid, the 88% solution was used, so at the 5% level, the actual amount of formic acid was 4.4%, and at 10% it was 8.8%.

The mode of action of the crystallization inhibitors identified in accordance with the present invention is not well understood. However, they probably function as kinetic crystallization inhibitors. Surprisingly, the crystallization inhibitors identified are not good solvents for trimethylolethane as compared to water. For example, the solubility of TME in methanol is only 75.2g/100g at 25° C. Interestingly and surprisingly, a number of compounds closely related to those found having crystallication inhibitory activity were tested but found to be inactive. Among compounds showing no crystallization inhibitory activity are ethanol, n-butanol, isobutyl alcohol, 2-butoxyethanol, diethylene glycol monoethyl ether, dipropylene glycol monomethyl ether, ethylene glycol, propylene glycol, and 1,3- and 1,4-butane diols. While it is believed that some form of hydrogen bonding process may be involved in trimethylolethane crystallization inhibition, the mechanism by which the process occurs is not known.

It should be pointed out that the effective crystallization inhibiting additives described herein do not totally prevent crystallization at all levels of supersaturation. The efficacy of the inhibitors is measured essentially in terms of delaying crystallization. Even with the most effective additives, TME crystallization could be effected at low temperature (high supersaturation levels) with seeding. Nonetheless, identification of crystallization inhibitors in accordance with the present invention offers a significant advantage for commercial manufacture and shipment of easily handled TME in bulk liquid form.

I claim:

1. A method for inhibiting crystallization of trimethylolethane from a supersaturated aqueous solution thereof comprising the step of adding to said solution having a concentration of about 50% or more of trimethylolethane or to an unsaturated solution of trimethylolethane which is at an elevated temperature but which would be supersaturated at ambient temperature, a crystallization-inhibitor compound selected from the group consisting of methanol and formic acid in an amount sufficient to provide a concentration of from about 4% to about 15% by weight of the solution and the water content is from about 40% to about 45%.

2. The method of claim 1 herein the crystallization-inhibitor compound is methanol.

3. The method of claim 1 wherein the crystallization-inhibitor compound forms about 10 percent by weight of the resulting crystallization-inhibited, supersaturated trimethylolethane solution.

4. The method of claim 1 wherein the crystallization-inhibitor compound is formic acid.

5. The method of claim 1 wherein the inhibitor is added to the solution while the solution is above saturation temperature.

6. The method of claim 1 wherein the inhibitor is added to the solution after it has become supersaturated.

* * * * *